United States Patent [19]

Desai et al.

[11] Patent Number: 5,912,354
[45] Date of Patent: Jun. 15, 1999

[54] PROCESS FOR PREPARING 4-AMINO-1,2,4-TRIAZOLIN-5-ONES

[75] Inventors: Vijay C. Desai, Shawnee; Klaus Jelich, Overland Park, both of Kans.; Hans Joachim Diehr; Reinhard Lantzsch, both of Wuppertal, Germany

[73] Assignees: Bayer Corporation, Pittsburgh, Pa.; Bayer Aktiengesellschaft, Leverkusen, Germany

[21] Appl. No.: 09/210,321

[22] Filed: Dec. 11, 1998

[51] Int. Cl.⁶ .................................................. C07D 249/12

[52] U.S. Cl. ........................................................ 548/263.8

[58] Field of Search ............................................ 548/263.8

[56] References Cited

U.S. PATENT DOCUMENTS

| 4,952,701 | 8/1990 | Müller et al. | 548/263.8 |
| 5,693,821 | 12/1997 | Diehr et al. | 548/263.8 |

*Primary Examiner*—Patricia L. Morris
*Attorney, Agent, or Firm*—Joseph C. Gil; Carol Marmo

[57] ABSTRACT

The present invention is related to an improved process for the commercial preparation of substituted aminotriazolinones, which are known intermediates in the preparation of herbicidal active compounds. In particular, this invention relates to the preparation of 4-amino-1,2,4-triazolin-5-ones, and more particularly to the preparation of 3-isopropyl-4-aminotriazolinone. The process of the invention includes reacting an oxadiazolinone with hydrazine hydrate in the absence of a solvent. In a preferred embodiment, the hydrazine hydrate is mixed with a basic compound, preferably aqueous sodium hydroxide.

12 Claims, No Drawings

PROCESS FOR PREPARING 4-AMINO-1,2,4-TRIAZOLIN-5-ONES

FIELD OF THE INVENTION

The present invention relates to an improved process for the commercial preparation of substituted aminotriazolinones, which are known intermediates in the preparation of herbicidal active compounds. In particular, this invention relates to the preparation of 4-amino-1,2,4-triazolin-5-ones, and more particularly to the preparation of 3-isopropyl-4-aminotriazolinone.

BACKGROUND OF THE INVENTION

It is known that substituted aminotriazolinones are obtained when corresponding oxadiazolinones are reacted with hydrazine hydrate in water. In U.S. Pat. No. 4,952,701, the oxadiazolinone is initially introduced in water and an excess of hydrazine hydrate is added to the reaction mixture at room temperature. The mixture is then heated and cooked. The excess hydrazine is removed by distillation and the desired aminotriazolinones are obtained. Due to the solubility of the aminotriazolinones in water, the resultant product is obtained in low yields and low purity; and therefore, an additional purification step is required.

Further, it is also known in the art that substituted aminotriazolinones are obtained when corresponding oxadiazolinones are reacted with hydrazine hydrate in the presence of a basic compound and in the presence of a polar organic solvent. Suitable basic compounds are in general inorganic or organic bases or acid acceptors. Such basic compounds include alkali metal or alkaline earth metal acetates, amides, carbonates, hydrogen carbonates, hydrides, hydroxides or alkoxides. Suitable polar organic solvents include dialkyl ethers, dialkyl ketones, nitriles, amides, esters, alcohols, and sulphoxides.

In U.S. patent application Ser. No. 08/696,013, the hydrazine hydrate is initially introduced in the basic compound and the polar organic solvent. The mixture is then heated to the required reaction temperature. As the mixture is cooked, the oxadiazolinone is slowly added until the reaction is complete. The desired aminotriazolinones are obtained by adjusting the pH of the mixture to about 7 by adding an acid and the organic solvent used in the initial step of the process. The solvent and water are removed by distillation and the desired product remains as a residue which is isolated by filtering. However, due to the solubility of the product in water, part of the desired product remains in the water and cannot be recovered. The work-up and isolation of the resultant product is extensive and the product is obtained in low yields.

In these known processes, the use of water or a solvent in the reaction mixture introduces excess water into the reaction and requires extensive purification procedures with resultant low yields. Thus, there is a need for an efficient process for preparing substituted aminotriazolinones, and in particular 4-amino-1,2,4-triazolin-5-ones, that produces a high net yield and high purity.

SUMMARY OF THE INVENTION

It is an object of the present invention to provide an improved process for the preparation of 4-amino-1,2,4-triazolin-5-ones of the general formula (I):

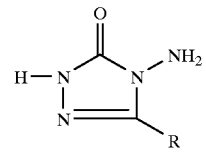

in which R
R represents a radical selected from the group consisting of an alkyl, alkoxy, alkylthio, alkylamino and dialkylamino, each of which is optionally substituted, by reacting an oxadiazolinone of the general formula (II):

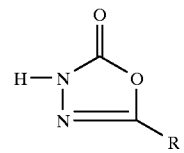

in which
R has the meaning indicated above, with hydrazine hydrate in the absence of a solvent. In a preferred embodiment, R represents an isopropyl group. Further, the reaction is preferably carried out in the presence of a basic compound. The reaction mixture is heated and cooked. The desired product is then isolated and purified using a mixture of a small amount of water in combination with an organic solvent. A preferred organic solvent is toluene.

DETAILED DESCRIPTION OF THE INVENTION

The process according to the invention relates to the preparation of 4-amino-1,2,4-triazolin-5-ones of the general formula (I):

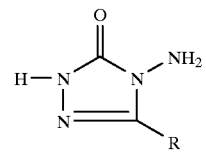

in which R
R represents a radical selected from the group consisting of an alkyl, alkoxy, alkylthio, alkylamino and dialkylamino, each of which is optionally substituted, by reacting an oxadiazolinone of the general formula (II):

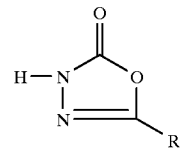

in which
R has the meaning indicated above,
with hydrazine hydrate in the absence of a solvent.

In a preferred embodiment, R represents an alkyl; the alkyl is preferably isopropyl. Further, in a preferred embodiment of the process, the hydrazine hydrate is mixed with a basic compound. Suitable basic compounds are in general inorganic or organic bases or acid acceptors. Such basic compounds include alkali metal or alkaline earth metal acetates, amides, carbonates, hydrogen carbonates, hydrides, hydroxides or alkoxides. A preferred basic compound for the present invention is aqueous sodium hydroxide. The molar ratio of hydrazine hydrate to oxadiazolinone is from about 1:1 to about 1.5:1, and preferably from about 1:1 to about 1.1:1. The molar ratio of the basic compound to oxadiazolinone is from about 0.05:1 to about 0.5:1, and preferably from about 0.075:1 to about 0.25:1. The mixture of hydrazine hydrate and basic compound are heated to a temperature of from about 100° C. to about 110° C., and preferably from about 102° C. to about 105° C. The oxadiazolinone of general formula (II) is then slowly added to the hydrazine hydrate and basic compound mixture. The oxadiazolinone is added over a time period of from about 20 to about 60 minutes, and preferably from about 30 to 40 minutes. This mixture is agitated for about 3 to about 5 hours at a temperature of from about 90° C. to about 110° C., and preferably from about 100° C. to about 105° C., until the reaction is complete. Following agitation and completion of the reaction, the mixture is cooled to from about 80° C. to about 100° C., and preferably from about 85° C. to about 90° C. Following cooling of the mixture, water and a solvent are added to the mixture. In a preferred embodiment, the water is added prior to the addition of the solvent. Preferably, the solvent is an aprotic, organic solvent. Such solvents are well known in the art. Such suitable solvents include toluene, methyl acetate, t-butyl methyl ether, methyl-isobutyl ketone, and ethyl acetate. Toluene is a preferred solvent for the process of the present invention. The amount of solvent used can vary over a wide range as readily determined by a skilled artisan. The precise amount of solvent will depend on the particular solvent used. Where toluene is the solvent, it is present in a molar ratio of toluene to oxadiazolone of from about 1:1 to about 8:1; and preferably from about 3:1 to about 4:1. The molar ratio of water to oxadiazolone is from about 1:1 to about 6:1; and preferably from about 1:1 to about 3:1. The mixture is then cooled to a temperature of from about 5° C. to about 20° C. and preferably from about 5° C. to about 10° C. A pH adjusting agent is added to the mixture to adjust the pH from about 5.0 to about 8.0, and preferably from about 6.0 to about 7.0. Suitable pH adjusting agents include hydrochloric acid, sulfuric acid, phosphoric acid, and acetic acid. In a preferred embodiment, concentrated hydrochloric acid or aqueous sulfuric acid is used as the pH adjusting agent. The molar ratio of acidic pH adjusting agent to oxadiazolone is from about 0.05:1 to 0.5:1.

The desired aminotriazolinone is isolated by distilling the water from the reaction mixture. The resultant residue is dissolved in water at about 75° C., cooled to from about 10° C. to about 20° C., and filtered. The filter cake is washed with ice water and subsequently dried at about 60° C. Further, the solvent phase is separated from the aqueous phase, and the solvent is recovered via distillation.

The following Examples illustrate preferred embodiments of the present invention and are not limiting of the specification and claims in any way.

EXAMPLES

EXAMPLE 1

Preparation of 3-Isopropyl4-Amino-Triazolinone Using a Mixture of Toluene and 20 ml of Water Approximately 53 g (1.05 mole) of hydrazine hydrate was charged to a flask. The hydrazine hydrate was agitated and then about 15.6 g (0.195 mole) of 50% sodium hydroxide (NaOH) solution was added. This mixture was heated to reflux and then about 132 g (1.0 mole) of isopropyl-oxadiazolinone was added via a funnel. The total time for addition of the isopropyl-oxadiazolinone was about 40 minutes. The reaction mixture was cooked at a temperature of about 105° C. for about 5 hours. Following completion of the reaction, the mixture was cooled to about 85° C. About 300 g (3.26 mole) of toluene and about 20 ml of fresh water was added to the mixture. The mixture was then cooled to about 10° C. The pH of the mixture was adjusted to about 7.0 by the addition of about 15 g (0.076 mole) of 50% sulfuric acid. The solids were recovered via filtering. The solids were then washed with about 100 ml of toluene and then with 2×20 ml ice-cold water. The solids were dried at a temperature of about 60° C. under vacuum. The toluene phase was then separated from the mother liquor and the toluene was recovered via distillation. The active ingredient (A.I.) of the product and net yield are shown in Table I.

EXAMPLE 2

Preparation of 3-Isopropyl-4-Amino-Triazolinone Using a Mixture of Toluene and 40 ml of Water The process as described in Example 1 was repeated, with the exception that following completion of the reaction and it being cooled to about 85° C., about 40 ml (instead of 20 ml) of fresh water was added with about 300 g (3.26 mole) of toluene to the reaction mixture. The results are shown in Table I.

EXAMPLE 3

Preparation of 3-Isopropyl-4-Amino-Triazolinone Using a Mixture of Toluene and 60 ml of Water The process as described in Example 1 was repeated, with the exception that following completion of the reaction and it being cooled to about 85° C., about 60 ml (instead of 20 ml) of fresh water was added with about 300 g (3.26 mole) of toluene to the reaction mixture. The results are shown in Table I.

EXAMPLE 4

Preparation of 3-Isopropyl-4-Amino-Triazolinone Using a Mixture of Toluene and 50 ml of Water The process as described in Example 1 was repeated, with the exception that following completion of the reaction and it being cooled to about 85° C., about 50 ml (instead of 20 ml) of fresh water was added with about 280 ml (instead of 300 g) of toluene to the reaction mixture. The results are shown in Table I.

TABLE I

| Run No. | Reaction Temp. (C.) | Reaction Time (Hrs.) | A.I. (%) | Net Yield (%) |
| --- | --- | --- | --- | --- |
| 1 | 103 | 4 | 96 | 93 |
| 2 | 103 | 3.5 | 97 | 91 |
| 3 | 103 | 4 | 98.3 | 89 |
| 4 | 103 | 4 | 98 | 90 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing 4-amino-1,2,4-triazolin-5-ones of the formula:

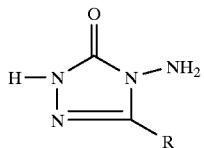

wherein

R represents a radical selected from the group consisting of an alkyl, alkoxy, alkylthio, alkylamino and dialkylamino, each of which is optionally substituted, comprising:

a) reacting an oxadiazolinone of the formula:

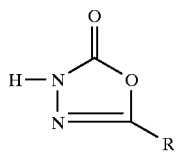

wherein

R has the meaning indicated above, with hydrazine hydrate in the absence of a solvent;

b) adding water and a solvent to the reaction product of step a), following completion of the reaction in step a);

c) adjusting the pH of the mixture of step b) to from about 5.0 to about 8.0 by the addition of an acidic material to allow the 4-amino-1,2,4-triazolin-5-ones to precipitate; and d) recovering the precipitate.

2. The process of claim 1 wherein R represents isopropyl.

3. The process of claim 1 wherein step a) is carried out in the presence of a basic compound selected from the group consisting of aqueous sodium hydroxide, alkali metal and alkaline earth metal acetates, amides, carbonates, hydrogen carbonates, hydrides, hydroxides, and alkoxides.

4. The process of claim 1 wherein the solvent used in step b) is an aprotic organic solvent selected from the group consisting of toluene, methyl acetate, t-butyl methyl ether, methyl-isobutyl ketone, and ethyl acetate.

5. The process of claim 1 wherein in step c) the pH of the mixture is adjusted to from about 6.0 to about 7.0.

6. The process of claim 1 wherein the acidic material used in step c) is selected from the group consisting of hydrochloric acid, sulfuric acid, phosphoric acid and acetic acid.

7. The process of claim 1 wherein the temperature in step a) is from about 90° C. to about 110° C., in step b) from about 80° C. to about 100° C., and in step c) from about 5° C. to about 20° C.

8. The process of claim 1 wherein in step a) the molar ratio of hydrazine hydrate to oxadiazolinone is from about 1:1 to about 1.5:1.

9. The process of claim 3 wherein the molar ratio of basic compound to oxadiazolinone is from about 0.05:1 to about 0.5:1.

10. The process of claim 4 wherein the molar ratio of toluene to oxadiazolinone is from about 1:1 to about 8:1.

11. The process of claim 1 step b) wherein the molar ratio of water to oxadiazolinone is from about 1:1 to about 6:1.

12. The process of claim 1 step c) wherein the molar ratio of acidic material to oxadiazolinone is from about 0.05:1 to about 0.5:1.

* * * * *